(12) United States Patent
Haverich et al.

(10) Patent No.: US 10,292,782 B2
(45) Date of Patent: May 21, 2019

(54) LIGHTING DEVICE FOR SURGICAL PURPOSES

(71) Applicant: CORLIFE OHG, Hannover (DE)

(72) Inventors: Axel Haverich, Hannover (DE); Kamil Nowak, Hannover (DE); Michael Harder, Hildesheim (DE)

(73) Assignee: CORLIFE OHG, Hannover (DE)

( * ) Notice: Subject to any disclaimer, the term of this patent is extended or adjusted under 35 U.S.C. 154(b) by 594 days.

(21) Appl. No.: 14/428,120

(22) PCT Filed: Sep. 16, 2013

(86) PCT No.: PCT/EP2013/069161
§ 371 (c)(1),
(2) Date: Mar. 13, 2015

(87) PCT Pub. No.: WO2014/041172
PCT Pub. Date: Mar. 20, 2014

(65) Prior Publication Data
US 2015/0250555 A1  Sep. 10, 2015

(30) Foreign Application Priority Data

Sep. 14, 2012  (DE) ........................ 10 2012 018 170

(51) Int. Cl.
*A61B 90/30* (2016.01)
*F21L 4/00* (2006.01)
(Continued)

(52) U.S. Cl.
CPC .............. *A61B 90/30* (2016.02); *A61B 90/53* (2016.02); *A61B 90/57* (2016.02); *F21L 4/00* (2013.01);
(Continued)

(58) Field of Classification Search
CPC ................................ A61B 90/30; A61B 90/35
See application file for complete search history.

(56) References Cited

U.S. PATENT DOCUMENTS 5,005,966 A * 4/1991 Handler ................... A61B 3/10
351/221
6,213,937 B1 * 4/2001 Vivenzio ................. A61B 1/267
600/193
(Continued)

FOREIGN PATENT DOCUMENTS

DE 12 38 572 10/1961
DE 94 10 886 7/1994
(Continued)

OTHER PUBLICATIONS

Office Action dated Jul. 4, 2017 for Japanese Application No. 2015-531591, filed Sep. 16, 2013.
(Continued)

*Primary Examiner* — Olivia C Chang
(74) *Attorney, Agent, or Firm* — Knobbe Martens Olsan & Bear, LLP

(57) ABSTRACT

The invention relates to a lighting device (100), which is equipped for fastening to a surgical instrument (200) or, by means of adapter (90; 91), to a body part (92), in particular a finger of a surgeon or of an operating room assistant, in order to serve as a light source during a surgical operation, in particular within a body cavity or organ cavity of genuine or traumatic origin and in other body regions that are difficult to access. At least one pin (20) pointing outward from the wall of the housing (10) is arranged on the housing (10) of the lighting device (100) in a wall area (30) directed toward the surgical instrument in the fastening position, which pin has a light emitting opening (40) at the distal end of the pin and is designed for passing through an opening (220) of the surgical instrument or of the adapter (90; 91)

(Continued)

and thus establishing a form-closed or force-closed connection to the opening. The pin (20) is preferably movable in order to achieve optimal illumination of the operation site. The invention further relates to a surgical instrument suitable for accommodating the lighting device (100) and a set comprising the lighting device (100) and at least one surgical instrument.

16 Claims, 10 Drawing Sheets

(51) Int. Cl.
*A61B 90/57* (2016.01)
*A61B 90/53* (2016.01)
*A61B 17/02* (2006.01)
*F21V 33/00* (2006.01)
*A61B 17/00* (2006.01)
*F21W 131/205* (2006.01)
*F21Y 115/10* (2016.01)

(52) U.S. Cl.
CPC ....... *A61B 17/02* (2013.01); *A61B 2017/0023* (2013.01); *A61B 2017/00438* (2013.01); *A61B 2017/00477* (2013.01); *A61B 2017/00734* (2013.01); *A61B 2017/00862* (2013.01); *A61B 2017/00876* (2013.01); *A61B 2017/00946* (2013.01); *A61B 2017/00951* (2013.01); *A61B 2090/309* (2016.02); *F21V 33/0068* (2013.01); *F21W 2131/205* (2013.01); *F21Y 2115/10* (2016.08)

(56) References Cited

U.S. PATENT DOCUMENTS

| | | | | |
|---|---|---|---|---|
| 6,379,296 | B1* | 4/2002 | Baggett | A61B 1/303 600/178 |
| 2004/0172105 | A1 | 9/2004 | Vankoski et al. | |
| 2007/0019400 | A1 | 1/2007 | Clausen et al. | |
| 2007/0103926 | A1 | 5/2007 | Brooks et al. | |
| 2007/0189004 | A1 | 8/2007 | Dickes et al. | |
| 2009/0097236 | A1 | 4/2009 | Miller et al. | |
| 2011/0164432 | A1 | 7/2011 | Wakaki et al. | |
| 2014/0275790 | A1* | 9/2014 | Vivenzio | A61B 1/303 600/197 |

FOREIGN PATENT DOCUMENTS

| | | |
|---|---|---|
| DE | 102 13 919 | 3/2002 |
| DE | 20 2004 00296 | 5/2004 |
| JP | 2002504832 A | 2/2002 |
| JP | 2002163901 A | 6/2002 |
| JP | 3098051 U | 2/2004 |
| JP | 2004290380 A | 10/2004 |
| JP | 2005071884 A | 3/2005 |
| JP | 2008 034209 | 2/2008 |
| JP | 2009523551 A | 6/2009 |
| JP | 2012146451 A | 8/2012 |
| WO | WO 1998/00069 A1 | 1/1998 |
| WO | WO 02/07632 | 1/2002 |
| WO | WO 2007/084641 A2 | 7/2007 |
| WO | WO 2009/137941 | 11/2009 |

OTHER PUBLICATIONS

International Search Report dated Dec. 16, 2013 for PCT Application No. PCT/EP2013/069161, filed Sep. 16, 2013.

\* cited by examiner

Fig. 8
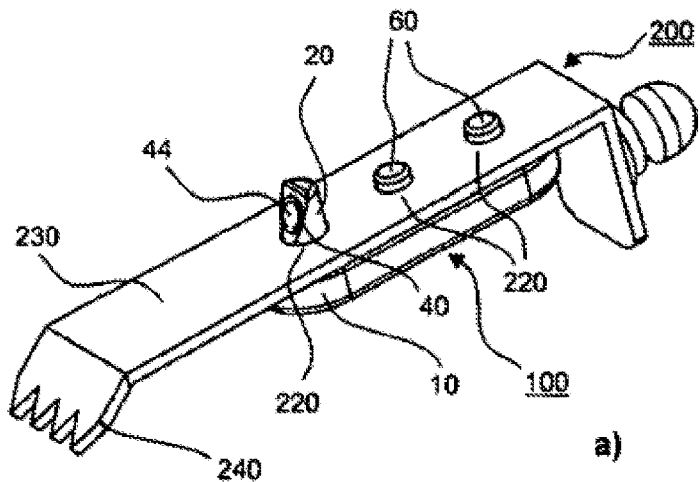
a)
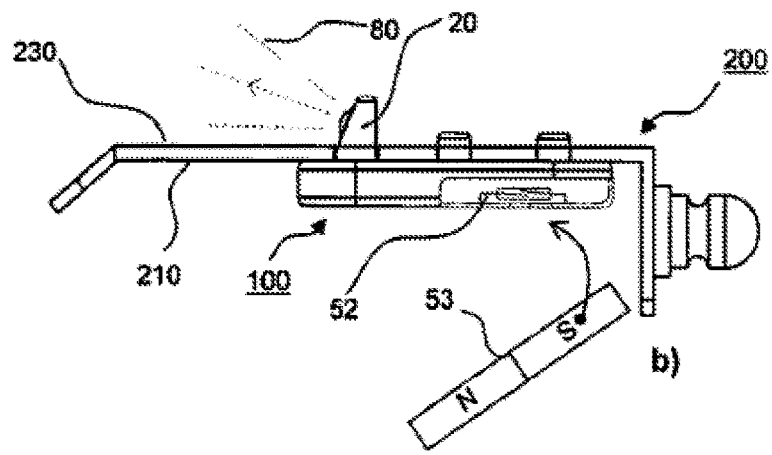
b)
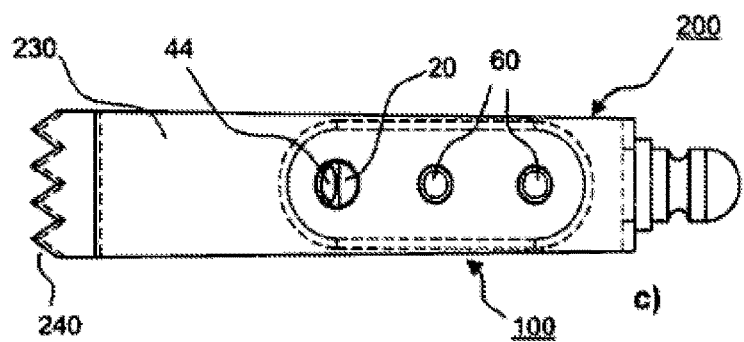
c)

Fig. 11
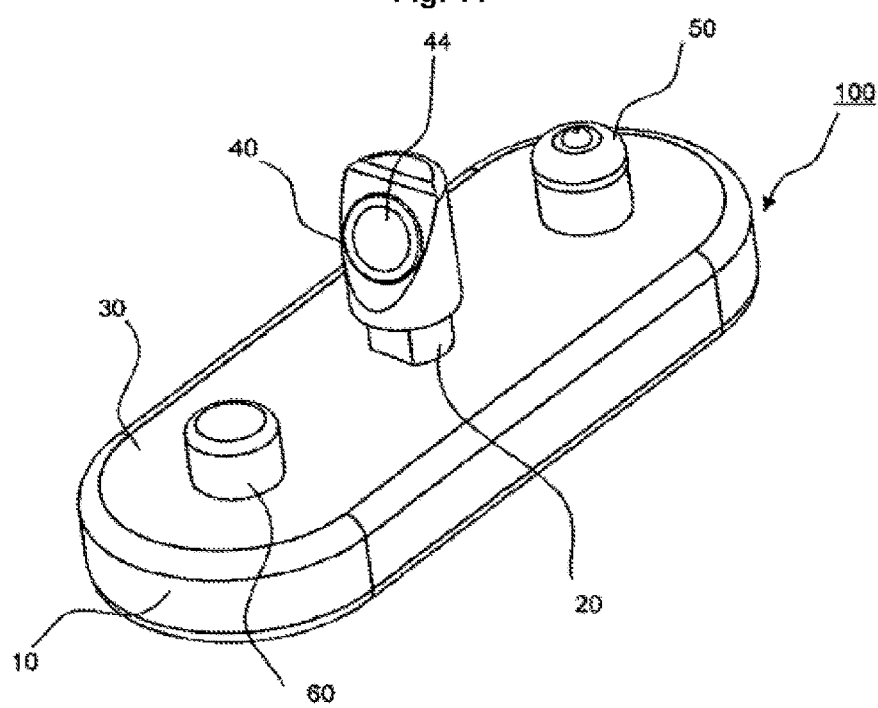
Fig. 12
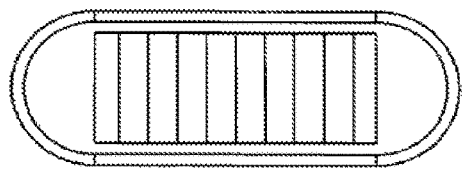
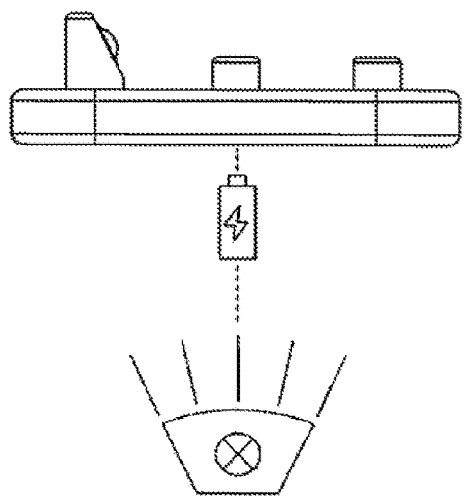

Fig. 14
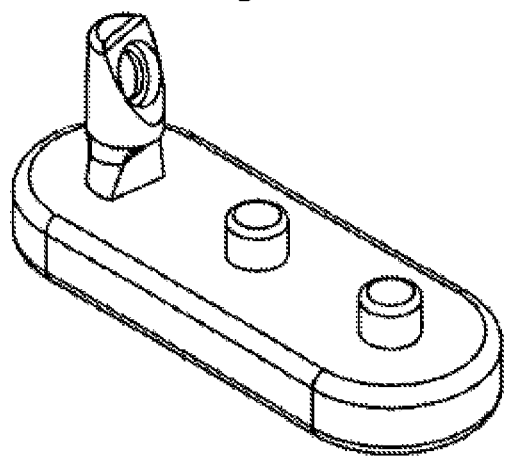
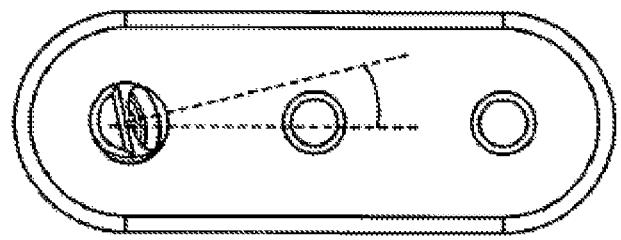
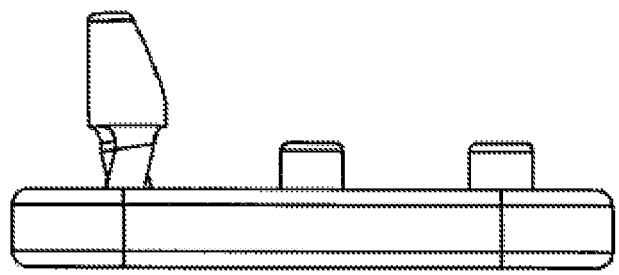

Fig. 15
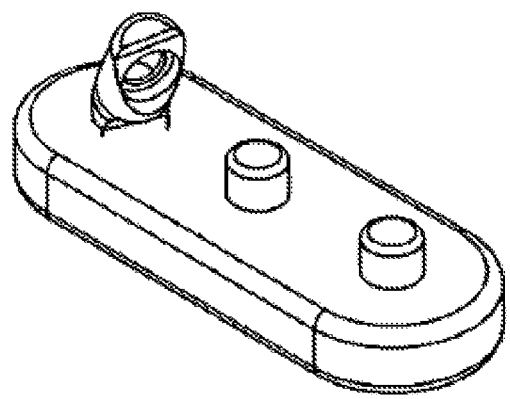
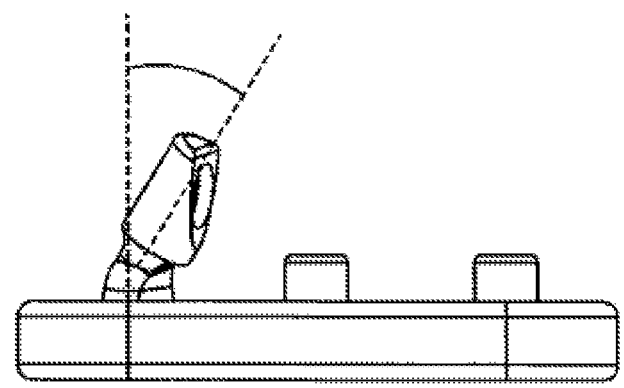
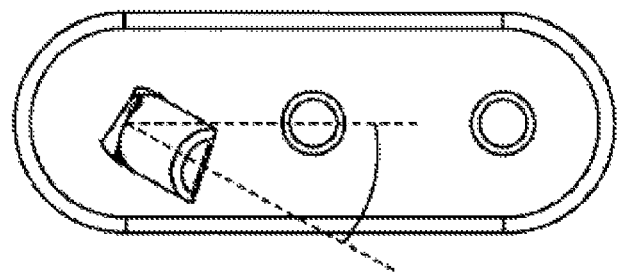

LIGHTING DEVICE FOR SURGICAL PURPOSES

The invention relates to a lighting device, which is equipped for fastening to a surgical instrument or by means of adapter to a body part, in particular a finger of a surgeon or of an OP-assistant, in order to serve as a light source during a surgical operation, in particular within a body cavity or organ cavity of genuine or traumatic origin and in other body regions that are difficult to access. Herein, at least one pin pointing outwards from the wall of the housing is arranged on the housing of the lighting device in a wall area directed towards the surgical instrument in the fastening position, wherein the pin has a light-emitting opening at its distal end and is designed for reaching through a fenestration of the surgical instrument or of the adapter and thus establishing a form-fit or force-fit connection with the fenestration. The pin is preferably movable in order to achieve optimal lighting of the operation site. The invention further relates to a surgical instrument suitable for the reception of the lighting device and a set comprising the lighting device and at least one surgical instrument.

DEFINITION OF TERMS

Herein, "surgical instruments" are all instruments, that are in particular required for surgical interventions by a surgeon. These include inter alia retractors, generally setting tools (spreaders), forceps, scalpels, clamps, drills, tubular shaft instruments, pliers, etc. Retractors are all devices and tools for keeping open the situs, such as, but not limited to, spreaders, retractor blades (blades), frames and tissue retractors.

A "fenestration" of a surgical instrument refers to at least one through hole on an instrument part.

A "set" refers to an arrangement of several instruments, devices or components that are in association to one another. A "set" is often referred to as a "kit". The set can be in a common packing unit for the items. According to the operation technique, it is also common that sets for certain operation techniques are assembled together. One packaging unit or a box, especially a sterile box, can include therein a variety of instruments, spare parts and additional parts that are required for a certain operation technique.

STATE OF THE ART

Ceiling lights, headlights and light guides are traditionally used for illumination of a surgical wound; however, they have significant drawbacks. Although ceiling lights provide a high luminous intensity, the shadow caused by the personnel working in the light cone cannot be prevented despite swiveling and rotating the light beam head. Especially for narrow and deep wounds the ceiling lights do not provide sufficiently good illumination. Headlights have a similar problem, since also here the light is coming from above, and they also have the disadvantage that only the surgeon can see enough. Furthermore, the freedom of movement of the surgeon is limited due to the wiring of many models. Additionally, wearing the oftentimes heavy headlights can be tiring. Both systems can also, in spite of infrared filters, lead to a strong heat development in the operating room. Although fiber optical devices such as light guides conduct no heat away, as they are equipped with a cold-light source, and also prevent shadowing from instruments and heads as they are used directly in situ, however, they are subject to an elaborate, expensive and ecologically unsound process of re-sterilization and the often already very limited manipulation field is additionally narrowed by them.

From US 2007/0189004 A1 a tubular lamp with light-emitting diode (LED) is known, which can be plugged in on the side of medical, laboratory and other instruments, in particular to gripping and cutting instruments such as tweezers and scissors. The lamp is supported by guide bushes that are part of the instrument, so that the lamp can only be used with such instruments. The power supply is realized via cables that need to be guided and handled with or in addition to the instruments, which can impair the function of the instrument and which is cumbersome and annoying for the surgeon. In particular, there is a danger that the lamp connected to the instrument may fall from the operation table due to the weight of the cables. In addition, this lamp is intended for re-sterilization.

The objective of the invention is to avoid the disadvantages of the prior art and to provide a preferably self-sufficient, space-saving lighting device which illuminates the surroundings of the instrument or the manipulation point contrasty, in true color and free of shade, without disturbing the conventional surgical procedure and without disturbing the function of the instrument to affect and changing its external shape substantially. It should further be a miniaturized lamp.

DESCRIPTION OF THE INVENTION

The objective is solved with the help of the lighting device according to claim 1, the surgical instrument according to claim 10 and the set according to claim 15. Advantageous developments of the invention are characterized in the dependent claims, the description and the figures.

The lighting device according to the invention having a housing and at least one illuminant is equipped for fastening to a surgical instrument, in order to serve as a light source during a surgical operation, wherein the housing has at least one pin pointing outwards from the wall of the housing in a wall area that is directed towards the surgical instrument in the fastening position, which
1. has a light-emitting opening at its distal end and
2. which is designed for reaching through a fenestration of the surgical instrument and thereby establishing a form-fit or force-fit connection, such as a clamping, locking, snap-in or force-fit or frictional engaged plug-in or press-fit connection.

The invention is suitable for illuminating chest cavity or abdomen, especially for surgeries on the heart, on the lungs or on other internal organs and for interventions in the field of surgical orthopedics. The lighting device is suitable for use in sterile premises, such as in operating rooms in hospitals, as well as interventions in less sterile environments, such as in a field hospital or in manufacturing facilities for microelectronics. The lighting device according to the invention is also suitable for the use in all areas where particularly narrow and deep openings are to be illuminated.

The pin of the lighting device according to the invention sticks out of a housing wall. Thus, the pin rests on a preferably plane surface and sticks preferably substantially perpendicular out of it. Here, the pin forms a protrusion, in order to reach through the fenestration, which is formed fittingly on an associated surgical instrument, and at the same time serves for fastening. The construction of the invention allows the emission of light, as seen from the perspective of the lighting device, to the other side of the fenestration. The light emission takes place from a fenestrated instrument part, wherein the lighting device itself is arranged behind this instrument part.

The present invention therefore relates to a lighting device (100) equipped for fastening to a surgical instrument (200) or by means of adapters (90, 91) on a body part (92) of a surgeon or an OP-assistant, for example on a finger, in order to serve as a light source during a surgical operation for the illumination of body- and organ cavities, with a housing (10) and at least one illuminant, characterized in that at least one pin (20) pointing outwards from the wall of the housing (10) is arranged on the housing (10) in a wall area (30) directed towards the surgical instrument in the fastening position, wherein the pin (20) has a light-emitting opening (40) at the distal end of the pin and is designed for reaching through a fenestration (220) of the surgical instrument or of the adapter (90; 91) and thus establishing a form-fit or force-fit connection with the fenestration.

The length of the pin from the basis on the housing wall to the lower edge of the light-emitting opening is preferably 5 mm to 10 mm.

The pin is shaped so that it can reach through a fenestration of the surgical instrument and thereby forming a force-fit or form-fit connection, which is preferably designed as a frictionally engaged plug connection or as form-fit snap-on hook. In general, the fenestration is designed so that in cooperation with the pin a clamping, locking, snap-in, plug-in or press-fit connection is realized. Preferably, the pin is substantially cylindrical, which, for example, comprises a pin bent in longitudinal direction and pins with a modified cross-sectional shape, for example, elliptical cross-sections. The pin preferably has a cylindrical or slightly conical outer wall with a small interference for forming a frictional plug-in connection to a corresponding drilled hole on the surgical instrument forming the fenestration. Basically, the plug-in connection is a fit. Basically, the plug-in connection can be formed by protrusions of any shape. Usually a slight excess of a few microns is sufficient. The plug-in connection should be designed so that the lighting device can only be removed with some force, so that it can be handled safely on the surgical instrument. Preferably, the plug-in connection is designed to withstand a tensile force of at least 10 N, more preferably at least 30 N.

Alternatively to a plug-in connection, a locking or snap-in connection may be provided, which means that the pin has a snap element, preferably one or more hooks, wherein said snap element engages in a locking manner the fenestration of the surgical instrument. Suitable locking mechanisms are known in the art and are not described further here.

A plug-in connection is preferred in order to remove the lighting device from the instrument in an easy and non-destructive way. The surgical instrument may be re-sterilized after removal of the lighting device, while the lighting device is preferably a disposable product.

The housing of the lighting device is preferably made of plastic or thin metal, and is in particular box-shaped or rod-shaped, and preferably designed flat. The lighting device according to the invention is as small as possible, so that the housing length for the currently used embodiments is preferably at most 100 mm, more preferably at most 70 mm, the housing width is preferably at most 50 mm, more preferably at most 40 mm and the housing height is preferably at most 25 mm, more preferably at most 15 mm. With these dimensions, the weight for a lighting device comprising a plastic housing and electronics is preferably below 25 g. The housing can be molded with the one or more pins in one piece.

The housing carries on the wall area directed towards the instrument part a protruding thin-walled attachment, referred to herein as a pin. The function of the pin has already been described above. The optical system of the lighting device is situated in the pin. The pin is preferably an essentially cylindrical stud having a light-emitting opening at its distal end, through which the light of the illuminant exits and which is preferably sealed with a translucent cover, made of a transparent plastic or glass. The cover is preferably formed as a lens in order to affect the light scattering.

The pin (20) of the lighting device (100) has the illuminant behind the light-emitting opening (40) in its distal end or in its head and is adapted to engage a fenestration of a surgical instrument. Preferably the fenestration is designed elongated or as an oblong hole so that the pin (20) is slidably movable in the elongated fenestration or the oblong hole. In order to illuminate the situs even better in a particularly preferred embodiment the pin (20) of the lighting device (100) is configured to be movable, which means that it can be bent and rotated.

In this particularly preferred embodiment the pin (20) is made at least partially from an elastic plastic, so that the pin (20) can be bent and rotated manually. Within the pin (20) the metallic wires extending from the power source to the illuminant act in addition to their function as electrical conductors also as core of the pin (20) and counteract the restoring forces of the elastic plastic and thus stabilize the manually set position of the pin (20) or more specifically of the head of the pin (20) with the light-emitting opening (40). Through this movability, the surgeon can adjust the light cone and thus illuminate the situs optimally.

The pliability from the vertical central position is preferably up to 30°, more preferably up to 40°, more preferably up to 50° and even more preferably up to 60° upwards and up to 30°, more preferably up to 40°, more preferably up to 50° and even more preferably up to 60° downwards. In addition, a capability of rotation from the vertical central position in a clockwise direction is up to 30°, more preferably up to 40°, more preferably up to 50° and even more preferably up to 60° as well as a capability of rotation from the vertical central position in a counter-clockwise direction is up to 30°, more preferably up to 40°, more preferably up to 50° and even more preferably up to 60°. Of course, all possible settings between these maximum values are possible, such as rotation by 15° in a clockwise direction and an upward bend of around 25° relative to the vertical central position. FIG. 13 shows in the middle the vertical central position and in the upper and the lower figure a downwardly inclined pin (20). FIG. 14 shows a rotated (counter-clockwise), but not inclined pin (20) and FIG. 15 shows a rotated and also inclined pin (20).

According to a preferred embodiment at least one light-emitting diode is located under the transparent cover or the lens. The pin is hollow to accommodate the illuminant and its supply wires. The components arranged within the pin may also be encapsulated by injection molding or cast.

Any light source that provides a sufficient light output to illuminate the surgical field can in principle serve as light source. Preferably, the light source has a light intensity of greater than or equal to 1500 mcd. It is a prerequisite for the use according to the invention that the desired luminous power is achieved by an illuminant that emits only so much heat that the surrounding tissue is not unnecessarily heated. Therefore, such light sources are preferably used which emit light with a very low proportion of infrared light (cold-light sources). Preferably light emitting diodes (LEDs) are used as light sources. Preferably one to ten light sources are arranged in a lighting device, in particular between one and ten LEDs.

By using LEDs as the light source infrared radiation is avoided, so that the wound cannot dry out. The heat delivered by the illuminat to the wires and emerging at the consumers is very low due to the high level of efficiency of the illuminant at sufficient illumination of the surgical field and due to the low power conversion of the circuit, so that also a heating of the tissue through the housing can be excluded.

The LED is preferably a white light LED. The LED is provided in SMD size (SMD=Surface Mounted Device) and is only a few millimeters in size. The LED is ideal for applications in the surgical field, because it reproduces the appearance of tissue and tissue fluid lifelike and contrastly due to its photometric parameters (CRI>85 (CRI color rendering index), color temperature=3000 K-6700 K). Through this genuine and faithful representation different types of tissue can be well distinguished from each other.

The outer shape of the lighting device is adapted in the area, which comes into contact with the instrument or which is adjacent to the instrument in the fastening position, preferably to the shape of the surgical instrument in the respective fastening area. In a preferred embodiment, this is done in a flush-mounted manner. Even if the wall area of the lighting device directed towards the surgical instrument is plane, this may be following the contour of the surgical instrument, if this is also plane there. The lighting device is adapted in its shape to the surgical instrument so that it does not impede the function and minimizes impairment of its outer shape.

According to a possible embodiment, only one pin is provided to fasten the lighting device on the surgical instrument, wherein said pin at the same time is provided with the only light-emitting opening of the illuminant. Alternatively, however, a plurality of pins may be provided, which reach through a plurality of fenestrations of the surgical instrument so that a plurality of light-emitting openings is provided.

According to a further embodiment it is intended that on the wall area of the housing in addition to the pin at least another fastening projection, in particular a nub or a round snap-in hook carrier is provided in allocation with a suitable holder on the surgical instrument.

The holder can be a fenestration, thus a opening, which would also be suitable for a pin, or any other suitable holder, such as a cut-out. A cut-out names here a non-continuous, i.e. not penetrating the wall of the instrument, otherwise shaped and extending slot or a blind hole.

The additional fastening projections serve to make the connection between lighting device and surgical instrument mechanically stronger and to increase the security against rotation, which can be particularly useful in a cylindrical fastening pin.

Also the strength of the connection can be increased by further additional measures. For example, adherent coatings can be formed on the adjacent surfaces of the lighting device and surgical instrument or the lighting device can be further fastened with an adhesive to the instrument. In a preferred development, it is provided that this is a pressure sensitive adhesive that can be easily removed after using the lighting device.

In a preferred embodiment of the lighting device (100) at least one further fastening projection (60) is provided, wherein one of said further fastening projections (60) is configured as a switch to turn the illuminant on and off, or besides the switching on and off to adjust the light intensity or brightness. FIG. 11 shows a lighting device (100) with a pin (20) in the center and an anterior fastening projection (60) and a posterior fastening projection (60), said posterior fastening projection (60) is configured as a switch. The posterior fastening projection (60) preferably consists of an elastic plastic material, or preferably coated with an elastic plastic material and is preferably designed as a pressure switch. For example, the illuminant can be switched on by pressing this switch once and switched off again by pressing it again. It is preferred, when the illuminant is switched on by pressing the switch once and by repeatedly pressing this switch the brightness is increased gradually up to a maximum and by continuing to press this switch the light intensity is again gradually reduced until completely being switched off. In another configuration of this switch a continuos pressing first turns the illuminant on and then increases its brightness as long as the switch remains actuated and upon reaching the maximum brightness, the light intensity is reduced again continuously as long as the switch is actuated up to turning off the illuminant. In this embodiment, the functions of turning on and off, or in addition, the adjustment of the brightness and the fixation of the lighting device (100) on the surgical instrument can be achieved elegantly by an additional switch configured as a fastening projection (60).

Thus, another advantageous embodiment of the present invention relates to a lighting device (100) equipped for fastening to a surgical instrument (200) or by means of adapters (90, 91) on a body part (92) of a person, in particular a finger, wherein the lighting device (100) comprises a housing (10) and at least one illuminant, characterized in that at least one pin (20) and a fastening projection (60) pointing outwards from the wall of the housing (10) are arranged on the housing (10) in a wall area (30) directed towards the surgical instrument in the fastening position, wherein the pin (20) has a light-emitting opening (40) at its distal end and contains an illuminant and the pin (20) is designed for reaching through a fenestration (220) of the surgical instrument or of the adapter (90; 91) and thus establishing a form-fit or force-fit connection with the fenestration and the fastening projection (60) is designed as a switch for turning the illuminant on and off.

The lighting device includes as power supply unit at least one accumulator, a battery or a combination of both energy sources. In the presently preferred embodiment, a accumulator is designed so that a light-emitting period of at least 60 minutes, more preferably of 120 minutes, especially preferably of several hours, is guaranteed. Preferably the near end of the operating time of the accumulator or the battery is indicated by an optical signal. In addition, it is preferred that by a control within the lighting device (100) the switching on is only possible within a predetermined period of time, so that reuse of the lighting device (100) after a predetermined time is no longer possible. Due to the internal power supply unit, an external cable routing is superfluous and possible hazards caused thereby are eliminated.

In a particularly preferred embodiment of the present invention, the internal power supply unit, for example a battery or an accumulator, is charged by a solar cell, which is arranged on the housing (10) of the lighting device (100). This embodiment has several advantages. First of all, no cables, which lead from the exterior into the lighting device (100) in order to charge the power supply unit, are required, which are cumbersome and also impose a sterility problem and are unable to completely seal the interior of the lighting device (100) and on the other hand, a sterile packaged lighting device (100) can be fully charged once again after prolonged storage before delivery to e.g. an hospital, so that the internal power supply unit has the maximum capacity upon use of the lighting device (100).

This is a huge advantage, since the lighting devices (100) are stored in sterile packaged manner and for example, during the storage for one year, the internal power supply unit could discharge half or almost fully. With a wired charging of the internal power supply unit, the sterile packaging would needed to be opened and the lighting device (100) would have to be re-packaged in a sterile manner after charging the internal power supply unit.

The charging of the internal power supply unit by a solar cell integrated in the housing (10) of the lighting device (100), however, can be effected through the sterile packaging without a need for opening the sterile packaging.

Normally, the lighting device (100) is packed sterile in a blister pack and preferably in a sterile package (for example, a primary blister made of thermoforming film) and a protective packing (for example, a secondary blister of similar materials as the primary blister). After packaging in a sterile room in one or two blister packs sterilization is preferably carried out using hydrogen peroxide plasma.

The irradiation of the solar cell integrated in the housing (10) of the lighting device (100) can be effected through the blister pack(s). The blister pack(s) are permeable to visible light or more generally to the radiation, which is required by the solar cell to produce electricity, so that a cable-free charging of the internal power supply unit by means of a solar cell irradiated through the sterile packaging can occur.

Thus, a particularly preferred embodiment of the present invention relates to a lighting device (100) in a sterile package, wherein the lighting device (100) contains an internal power supply unit, and at least one solar cell is integrated in the housing (10) of the lighting device (100) and the sterile packaging allows the passage of radiation which is required by the solar cell for producing electricity.

In other words, the particularly preferred embodiment relates to a lighting device (100) in a sterile package, wherein the lighting device (100) has an internal power supply unit and an illuminant and at least one solar cell is integrated into the housing (10) of the lighting device (100), wherein the at least one solar cell serves for the charging of the internal power supply unit and the sterile packaging allows the passage of radiation, which is required by the solar cell for producing electricity in order to charge the internal power supply unit.

A further preferred embodiment is directed to a lighting device (100) equipped for fastening to a surgical instrument (200) or by means of adapters (90, 91) on a body part (92) of a person, in particular a finger, wherein the lighting device (100) comprises a housing (10) and at least one illuminant, characterized in that at least one solar cell is integrated in the housing (10) and at least one pin (20) pointing outwards from the wall of the housing (10) is arranged on the housing (10) in a wall area (30) directed towards the surgical instrument in the fastening position, wherein the pin (20) has a light-emitting opening (40) at its distal end and is designed for reaching through a fenestration (220) of the surgical instrument or of the adapter (90; 91) and thus establishing a form-fit or force-fit connection with the fenestration. Herein, the solar cell serves to charge an internal power supply unit within the housing such as for example of a battery or of an accumulator. The illuminant is also located preferably within the pin (20) or preferably within the pin (20) and behind the light-emitting opening (40).

In all embodiments described herein, the pin (20) and the optional fastening projections (60) are connected to the housing (10) of the lighting device (100) in a sealing manner and the light-emitting opening (40) in the pin (20) is sealed, for example, with a lens or a translucent material such as glass or plastic, so that no liquid, and preferably also no gas can penetrate into the interior of the lighting device (100).

An even further preferred embodiment is directed to a lighting device (100) equipped for fastening to a surgical instrument (200) or by means of adapters (90, 91) on a body part (92) of a person, in particular a finger, wherein the lighting device (100) comprises a housing (10), an internal power supply unit and at least one illuminant, characterized in that at least one solar cell is integrated in the housing (10) and at least one pin (20) pointing outwards from the wall of the housing (10) is arranged on the housing (10) in a wall area (30) directed towards the surgical instrument in the fastening position, wherein the pin (20) has a light-emitting opening (40) at its distal end and is designed for reaching through a fenestration (220) of the surgical instrument or of the adapter (90; 91) and thus establishing a form-fit or force-fit connection with the fenestration and the solar cell serves to charge the internal power supply unit.

An again further preferred embodiment is directed to a lighting device (100) equipped for fastening to a surgical instrument (200) or by means of adapters (90, 91) on a body part (92) of a person, in particular a finger, wherein the lighting device (100) comprises a housing (10), an internal power supply unit and at least one illuminant, characterized in that at least one solar cell is integrated in the housing (10) and at least one pin (20) pointing outwards from the wall of the housing (10) and a fastening projection (60) are arranged on the housing (10) in a wall area (30) directed towards the surgical instrument in the fastening position, wherein the pin (20) has a light-emitting opening (40) at its distal end and is designed for reaching through a fenestration (220) of the surgical instrument or of the adapter (90; 91) and thus establishing a form-fit or force-fit connection with the fenestration and the fastening projection is designed as on and off switch for the illuminant and the solar cell serves to charge the internal power supply unit.

In addition, is particularly preferred that the embodiments of a lighting device (100) with solar cell, as disclosed herein, are in a sterile package.

The illuminant of the lighting device is preferably activated by an external magnet brought into close proximity to a magnetic switch installed in the housing, which is known to the skilled person as a reed contact or reed switch.

Alternatively, a manually operable switch can be arranged on the housing of the lighting device, as in conventional lamps, by which the illuminant or the illuminants can be connected to the power supply, or again separated therefrom. A combination of magnetic switch and a manually operable switch is also possible.

Preferably pressure switches or buttons are used, which are arranged in a particularly preferred embodiment on the wall area of the housing that is directed to the surgical instrument, so that the pressure switch or button is activated when fastening the lighting device due to a contact with the adjacent instrument part. This embodiment is particularly suitable for a lighting device for a single use. Simultaneously with the fastening, the lighting device is switched on and gives light until it is removed again, or until the power supply ceases.

The lighting device according to the invention may be equipped with additional components. These include in particular 1. a compensation element between the wall area of the housing of the lighting device and the wall area of the surgical instrument, which
   a) enables or improves the adaptability of the lighting device to uneven instrument surfaces and
   b) increases the strength of the connection between the surgical instrument and the lighting device in order to prevent a breaking off of the pin or of the fastening projections during stress, for example by pressure or shearing forces,
2. an adapter, which is enables the fastening of the lighting device on a body part of the surgeon or of an OP-assistant, for example, on a finger.

The compensation element is primarily intended to create a compensation between the plane housing wall area of the lighting device and the uneven shaped, domed or grooved surface of a surgical instrument. Compensation elements can preferably comprise one or more spring clip(s), a membrane sheath or an elastic or soft filling material, for example from foam material. The compensation elements can fulfill additional functions. A membrane sheath protects the device, for example, simultaneously from moisture.

A preferred embodiment of the compensation element is a spring clip. The spring clip is preferably made of a plurality of metallic, longitudinal and transverse leaf springs that can be attached to the wall area of the housing of the lighting device in a locking, snap-in, or adhesive manner. When attaching the lighting device on for example a retractor blade, the leaf springs are deflected correspondent to the shape of the surface of the instrument and are adapted to it and remain in a tensed position, so that the lighting device can also be mounted on uneven blade surfaces. Due to their spring-back properties and their biased storage the tense leaf springs then counteract the forces that act on the lighting device, e.g. tissue forces, and fix the lighting device securely to the back of the retractor blade. In order to better withstand the spring pressure the spring clips are preferably used together with locking, or other form-fit fastening projections and/or pins.

A further preferred embodiment of the compensation element is a membrane sheath. The membrane sheath consists of a flexible and soft plastic. The adaptation to the surface of a particular surgical instrument happens via the design of the surface of the wall area of the membrane sheath, so that this corresponds to the surface of the instrument. The assembly of the membrane sheath on the lighting device is preferably accomplished by a snap-in, locking or adhesive connection.

The adapter for fastening the inventive lighting device on a body part or on another part or object can be constructed in various ways.

According to a first embodiment it is intended that the adapter has the form of an adapter ring. The adapter is designed similar to a finger ring, that can be put on via a ring-shaped or clasp-shaped part around a finger and which carries on the ring part a holder for the lighting device. This holder may have the form of and open, slotted box in which the lighting device can be inserted.

According to a further embodiment, the adapter may be formed as a strap, which is preferably a Velcro tape or strap with a Velcro tape endings having appropriate holders for the lighting device. In a preferred embodiment, the Velcro tape has at least one opening through which the pin of the lighting device is inserted from the inside to the outside, whereafter the strap is wrapped around a finger or another suitable object for fastening and is closed.

Other additional components and components of the device are not excluded and may additionally be attached to the lighting device.

The object of the invention is also achieved by a surgical instrument having at least one fenestration, arranged in a thin blade, a shaft, a tool housing, a handle and a flat or grooved formed leg of the instrument, and is designed for a form-fit or force-fit connection with a pin of the lighting device according to the invention.

A thin blade is to be understood as being designed in a sheet-shaped or plate-shaped, but not necessarily in a plane manner. The thickness of such a blade is preferably not more than 5 mm, more preferably not more than 2 mm, in particular not more than 1 mm. The blade is fenestrated so that the stud of the lighting device, which must at least be so long that it extends through the blade at the position of the fenestration, can be inserted through the fenestration opening of the blade, wherein the fastening device abuts behind or on the back of the blade with the wall area from which the pin points outwards. The pin protrudes beyond the fenestration opening in a way that the emission can still take place from the light-emitting opening, so that the light emission takes place from the front of the blade. The same applies to other thin or sheet-shaped or plate-shaped instrument parts. This can be, for example instrument housings, shafts, handles, legs, or the like.

Preferably, the surgical instrument provided with the fenestration for fastening the lighting device of the invention is a forceps, a clamp, a scalpel, a drill, a pair of pliers, a tubular shaft instrument, in particular a retractor, a blocker or a spreader, or a multi-part retraction system. The retractor blades or blades of such retractors or spreaders are formed flat and thin, so that the lighting device, which in this case preferably has the shape of a flat box, can be placed behind the blade in a flat manner and be easily penetrated in a fenestration by the pin.

The fenestration in the surgical instrument is designed to fit to the pin of the lighting device and is a corresponding through hole in the form of a drill hole, an oblong hole or an otherwise shaped opening so that a form-fit or force-fit connection with the pin of the lighting device can be established.

The fenestration is naturally always formed at a certain part of the instrument, frequently at a part of the instrument substantial for the function. This may be in particular blades, also referred to as sheets or holding sheets, handles or instrument legs which are preferably provided in a sheet-shaped or grooved or bulged form. Similarly, flat legs, or blades, for example of forceps, needle holders, clamps or pliers are well suited for the fastening of the lighting device according to the invention. Also housing parts of a complex instrument, fenestrated tube shafts or shafts of the distal end of handles, are well suited for the fastening of the lighting device according to the invention. Furthermore, it is possible to attach essentially rod-shaped miniaturized lighting devices in grooves that can be found in surgical instruments, such as in grooved legs of forceps, pliers or the like.

It is also possible to attach the lighting device on a body part, for example on a finger of a person.

In an advantageous development of the invention, the surgical instrument or the instrument part also has at least one suitable holder for fastening projections of the lighting device, in particular at least one non-continuous milling. The fastening projections can also engage in continuous fenestrations, as they are provided in the instrument in any case for inserting pins with light-emitting opening.

If the surgical instrument, such as a retractor blade, is present in fenestrated form, the fenestration is designed in a preferred embodiment as a through hole or a drilled through hole and is suitable for holding exactly one lighting device. Alternatively, the retractor blade can have a multiple of the required fenestrations that are positioned at some distance from each other, so that the lighting device can be placed as needed—it can be moved from a drilled through-hole to another drilled through-hole—so that a device having a plurality of pins with light-emitting openings can be used or so that a plurality of lighting devices can be fastened on an instrument.

The surgical instrument may be fenestrated with oblong holes, so that the lighting device can be moved back and forth and aligned to the instrument. The width of the oblong hole may preferably be matched to the diameter of the pin in a way that in each position of the pin relative to the oblong hole, in particular if the pin is formed as a cylinder, a plug-in connection by frictional forces is established.

According to a further embodiment, the holder of the lighting device may be milled in the surgical instrument so that it is equipped, for example, with continuous slots. The lighting device can be moved as in the fenestration with oblong holes, except that the width of each oblong hole from one to the other end of the hole decreases steadily and forms a cone-shaped slot, so that the lighting device is inserted loosely with the pin at one end of the slot and can be clamped by moving the pin within the slot.

The holders for additional fastening projections can be designed either as continuous fenestrations or non-continuous cutouts (depressions, grooves, blind holes).

The object of the invention is further solved by a set in which at least one lighting device according to the invention and one or more surgical instruments and/or instrument parts are provided, wherein at least one is fenestrated in order to connect to the lighting device. Additional instruments or instrument parts, additional parts, spare parts and auxiliaries can be present in the same set. Particularly preferred is a set that includes a collection for a particular operation technique. Thus, all the necessary resources for the implementation of a particular operation technique are given the surgeon at hand. The set may preferably be a packing unit.

In a further development of the invention, the set may contain in addition at least an adapter for the fixation of the lighting device on a body part and/or a compensation element for the contact between the wall of the lighting device and the wall of the instrument.

The advantages achieved by the invention reside in the targeted illumination of the surgical field without body parts or objects interfering with the light path and thereby creating a shadow on the surgical field, as it is the case with conventional surgical lights, because the lighting device according to the invention is located in the wound and since only the light emitting pin of the lighting device mounted to the rear side of the surgical instrument, which pin reaches through the fenestration, extends only a few millimeters into the wound.

A particular advantage of the lighting device lies in the fact that the surgical field can be optimally illuminated even with small wound openings, since the lighting device requires little space, since the main components of the lighting device such as the housing with illuminant, switches, wires, control and accumulator are nowadays available in miniaturized form. A restriction of the surgical field does not happen, because the lighting device is arranged on the rear side of a surgical instrument, so that none of its components permanently obstructs the surgical access.

Besides the small geometric dimension, the lighting device has a low weight so that it does not interfere with the function of the surgical instrument and the surgical procedure after the fastening to the surgical instrument, also because of its positioning on the rear side.

A further advantage of the lighting device is that it can be designed as a disposable article, whereby a cost- and time-consuming re-sterilization and thereby also the multiple use of hazardous and environmentally objectionable gases and chemicals is avoided. The lighting device according to the invention is also made of recyclable materials and contains in accordance with Directive 2011/65/EU (RoHS2) no electronic components with hazardous and noxious substances.

The lighting device can be fastened with little effort, even within the course of the surgical procedure.

DESCRIPTION OF THE FIGURES

FIG. 8 a further embodiment of a retractor blade with mounted lighting device with modified pin arrangement a) in perspective view, b) in side view, c) from above.

FIG. 11 depicts a preferred embodiment of the lighting device (100) with a pin (20) and two additional fastening projections (60), wherein one fastening projection (60) is at the same time designed as switch in order to switch the illuminant on and off as well as to optionally regulate its light intensity (brightness or brightness level).

FIG. 12 depicts a preferred embodiment of the lighting device (100) with a pin (20) and two additional fastening projections (60) and a solar cell at the bottom side of the housing (10) of the lighting device (100). The solar cell is integrated into the transparent housing (FIG. 12, top). The solar cell serves for charging an accumulator or a battery inside the housing (10), which then in turn serves as power source for the illuminant in the head of the pin (20). In FIG. 12 (down) a charging lamp with emitted radiation is depicted, which is directed towards the solar cell, which then produces electricity for charging the internal power supply unit.

FIG. 14 depicts from different viewing angles a pin (20) rotated about 10° counter-clockwise. The pin (20) is just rotated but not also bent at the same time.

FIG. 15 depicts from different viewing angles a pin (20) bent downwards or forwards as well as rotated clockwise.

EXAMPLES

The invention is explained in the following on the basis of examples that are depicted in the figures.

This shall solely serve for a better understanding of the invention without the invention being limited to the examples shown. Because of its general professional knowledge, the person skilled in the art can find further examples with the aid of the foregoing description.

Figure 1:
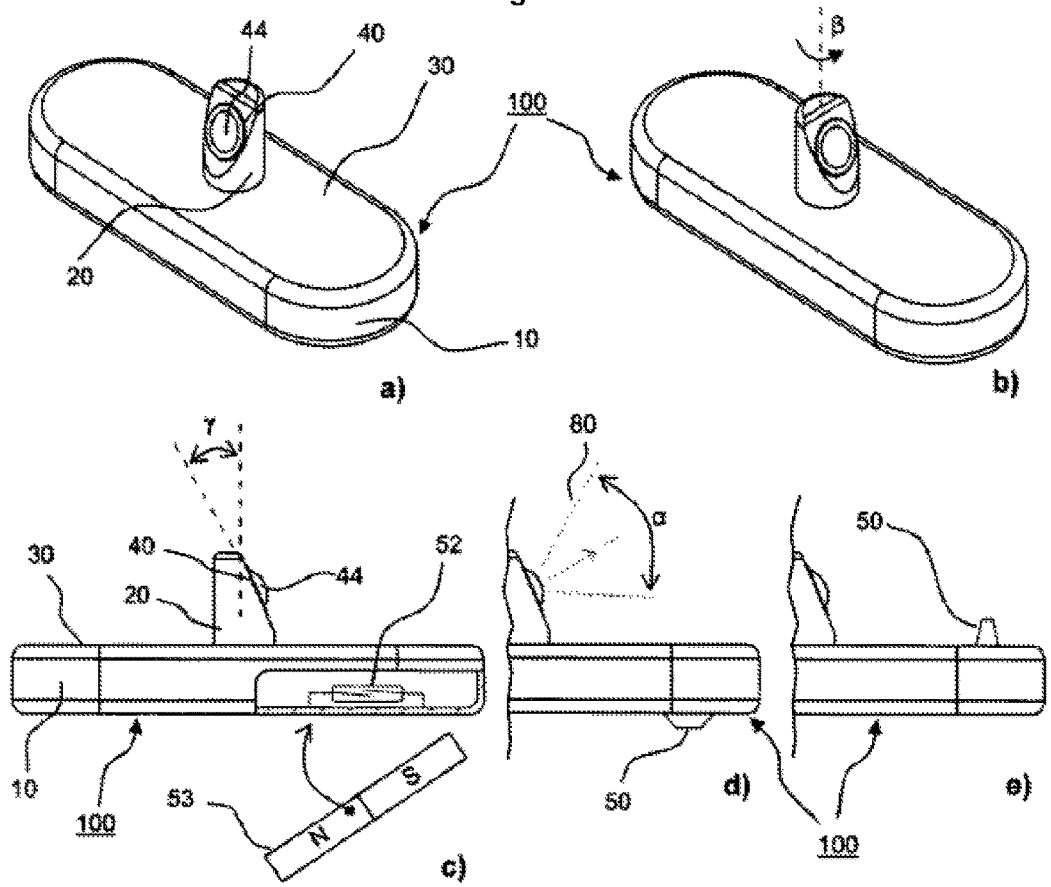
FIG. 1 a first embodiment of the fastening device with a box-shaped housing a) in perspective, b) in perspective with rotated pin (angle β, c) in side view with magnetic switch, d) in partial side view with press switch on the housing's rear side, e) in partial side view with press button or press switch on the wall area of the housing's front side.

FIG. 1 depicts a first embodiment of the lighting device 100 with a box-shaped housing 10, which carries a pin 20 here designed cylindrical and angled. Here, the housing 10 is produced together with the pin 20 and translucent cover 44 from a biocompatible plastic. The housing 10 has a wall area 30, which—during use of the lighting device 100 on a surgical instrument—is in contact at least with parts of its outer contour with a part of the instrument. The pin 20 being a protrusion from the housing 10 requires a fenestration in the not illustrated instrument and is located within the area limited by the the wall area 30. It can be recognized from the view in perspective according to FIG. 1a) that the pin 20 with light-emitting opening 40 is located centered in relation to the housing's front side with the wall area 30. It can be recognized from the side view according to FIG. 1c) that the front wall of the housing 10 with the wall area is designed plane. Due to its cylindrical shape the pin 20 clamps optimally by means of frictional connection both in circular drilled holes and in oblong holes, which can be formed as fenestrations in the non-illustrated instrument, or in other openings present on the instrument. In the illustrated example the light-emitting opening 40 sealed by a translucent cover or a lens 44, behind which a LED is located. The lens 44 is an attachment on the pin 20 that ensures a good diffusion of light to the surrounding. The exit angle of the light for this example is designated with alpha ($\alpha$). It can be seen in FIG. 1c) that the plane of the light-emitting opening can be tilted through a cant of the pin by an angle gamma ($\gamma$) with respect to the pin axis, whereby the light is directed more pointedly to the surgical area. The perspective view in FIG. 1b) depicts the lighting device 100 with a pin 20 rotated by the angle $\beta$ for elongated versions of retractor blades. FIG. 1) also displays a magnet 53 that activates a magnetic switch 52 placed inside the lighting device 100 upon approaching the housing 10 and thereby switches the herein not visible illuminant on, whose beam of light 80 exits the lighting device through the translucent cover 44 in the angle $\alpha$.

In addition to that, a press switch 50 sealed by a membrane can be seen in FIG. 1d), which—in relation to the light-emitting opening 40 located on the front side on the pin 20—is located at rear side of the housing 10. With the aid of this switch the mounted lighting device is switch on manually. The embodiment according to FIG. 1e) has a pushbutton switch 50, which is located next to the pin 20 within the area of the wall area 30. In this embodiment the wall area 30 aligns itself in a flush-mounted way to a plane retractor blade, so that the pushbutton switch 50 is automatically pressed upon fastening of the lighting device 100 to the not illustrated surgical instrument and the illumination is thereby switched on.

The embodiment shown is a simple lighting device producible on the small-scale with only one pin and one light source, namely a light-emitting diode covered by a lens 44, which can be attached to a not illustrated surgical instrument, if a fitting fenestration is provided for this in a thin part of the instrument, such as for example a retractor blade, which must not be thicker than the height of the pin 20.

In most figures the inwards of the lighting device, except for the magnetic switch 52, is not illustrated. Therein located are the power supply by means of battery and/or accumulator including associated wires to the illuminant and to the switch as well as other components of the circuit.

Figure 2:
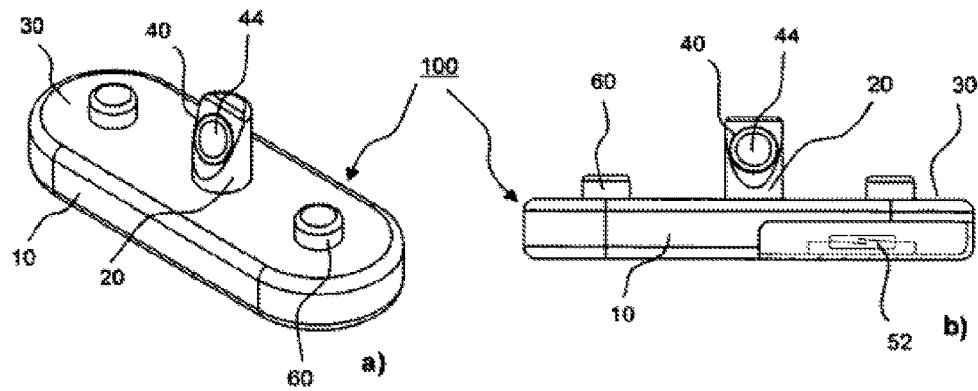
FIG. 2 a second embodiment of the fastening device with magnetic switch and nub as anti-twist safeguard a) in perspective, b) in side view.

FIG. 2 shows a similar embodiment, that is shown in FIG. 2a) in the perspective from the front and in FIG. 2b) from the side. The housing 10 of the lighting device 100 is formed as in FIGS. 1a) and 1c), the pin 20 attached as a clamp projection on the front side of the housing 10 is also designed cylindrical and provided with a translucent cover 44. The cover 44 is herein a simple converging lens so that the exit angle alpha ($\alpha$) of the light cone 80 is smaller in this example than shown in FIG. 1, which increases the luminous intensity in case of the same luminous flux. This causes a targeted and strong illumination of the illuminated surgical area. The embodiment of FIG. 2 additionally comprises two fastening projections 60 in the form of nubs as anti-twist safeguard and as an additional fastening mechanism. The nubs 60 engage in one or more recess(es) of the not illustrated instrument part, while the pin 20 reaches through a fenestration of the instrument part, wherein this can again be a circular drilled hole or a oblong hole. The diameter of the pin 20 is formed with a slight oversize to the drilled hole or to the width of the oblong hole on the instrument. The nubs 60 may also have a slightly enlarged diameter compared to the drilled hole of the surgical instrument and be designed as fit with little interference. The embodiment of FIG. 2 also has an internal magnetic switch 52 visible in FIG. 2b), which turns on the lighting device 100 by the application of a magnetic field, not illustrated here, for example of a magnet 53.

Figure 3:
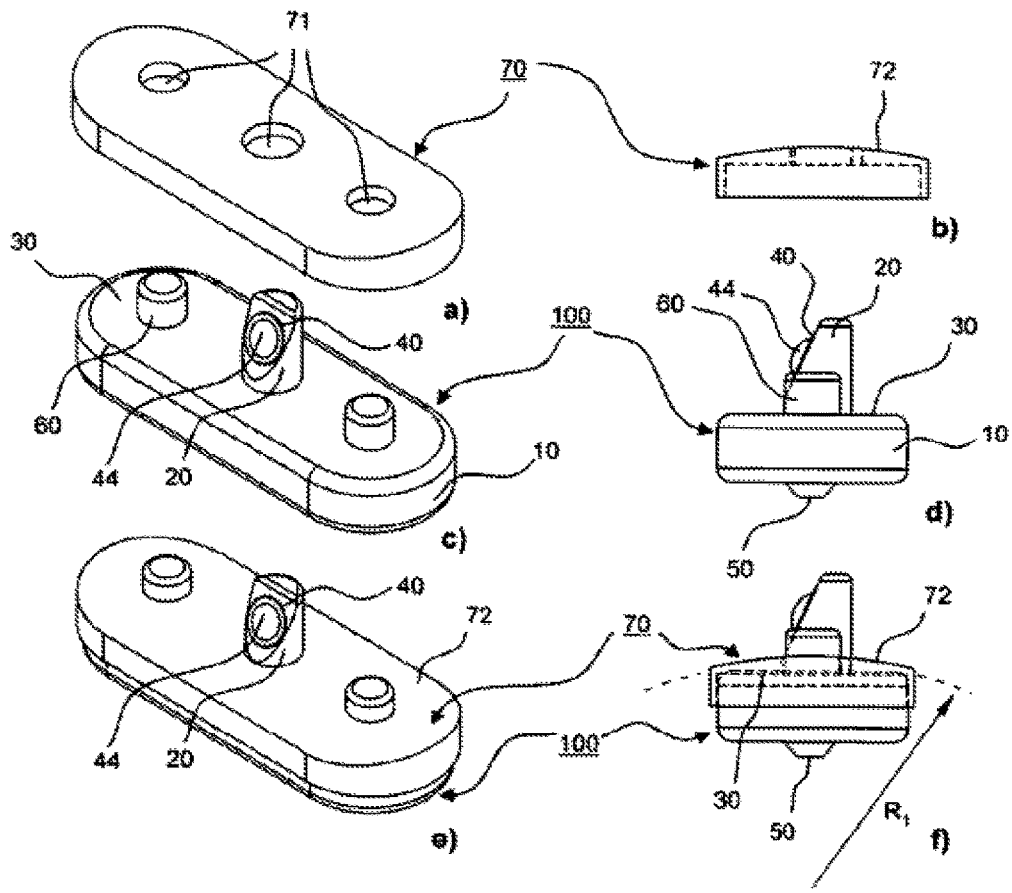
FIG. 3 the embodiment from FIG. 2. c) in perspective and d) in side view complemented by a membrane sheath: a) in perspective, b) in side view, plugged together: e) in perspective and f) in side view.

FIG. 3 depicts the lighting device 100 of FIG. 2, and as such again in FIG. 3c) in perspective and in FIG. 3d) from the side. FIG. 3a) and FIG. 3b) show a) in perspective and b) from the side a corresponding membrane sheath 70, which can be plugged into the lamp 100, as shown in FIG. 3e) in perspective and in FIG. 3F) from the side. This lighting device carries a switch 50 on the rear side that can be operated by hand or with a pointed object, such as a pair of tweezers. The membrane sheath serves as a compensation element, which enables the adaptation of the plane surface of the wall area 30 of this embodiment to a rounded rear side of a retractor blade. The adaptation to a certain version of retractor blade is herein achieved due to the dimensioning of the radius $R_1$ of the wall area 72 of the membrane sheath 70, which corresponds to the curvature radius of the respective retractor blade. The membrane sheath 70 is provided with fenestrations 71, which correspond with the pin 20 and the nubs 60 of the lighting device, which allows the assembly of the membrane sheath to the lighting device 100. The membrane sheath is herein only mounted and snaps or locks in laterally on the housing 10. In another embodiment, not shown here, the connection of membrane sheath and housing 10 may also be achieved in an adhesive manner.

Figure 4:
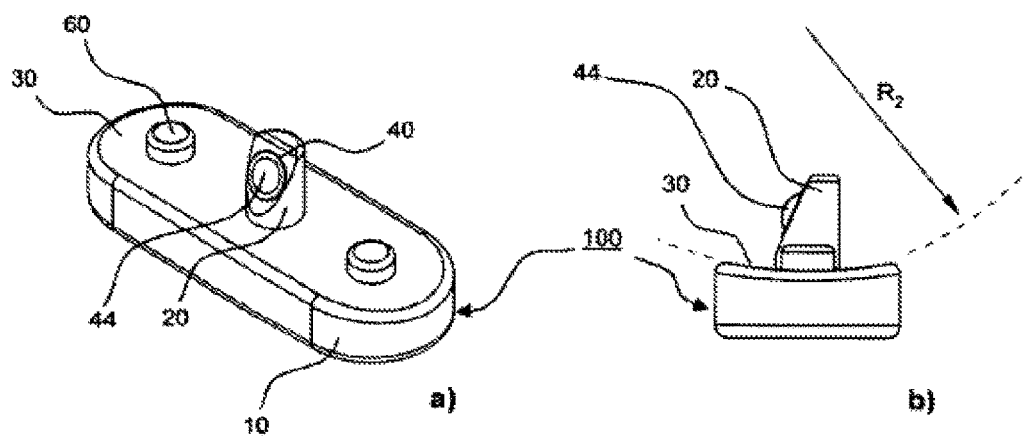
FIG. 4 a fourth embodiment with front wall shaped in adaption a) in perspective, b) in side view.

FIG. 4 shows another modified embodiment, in which the wall 30 of the housing 10 of the lighting device 100 is curved inwardly. This lighting device 100 may for example be attached to the inside of the handle of pliers, wherein the external shape of the lighting device 100 is adjusted by the inwardly curved front face carrying the pin 20 to the shape of a protrusion in the leg of the instrument and attacks this protrusion in a flush-mounted manner. The drawn radius $R_2$ of the outer wall area 30 of the housing 10 of the lighting device 100 is adapted precisely to the rear side of the bulged surface of a surgical instrument.

Figure 5:
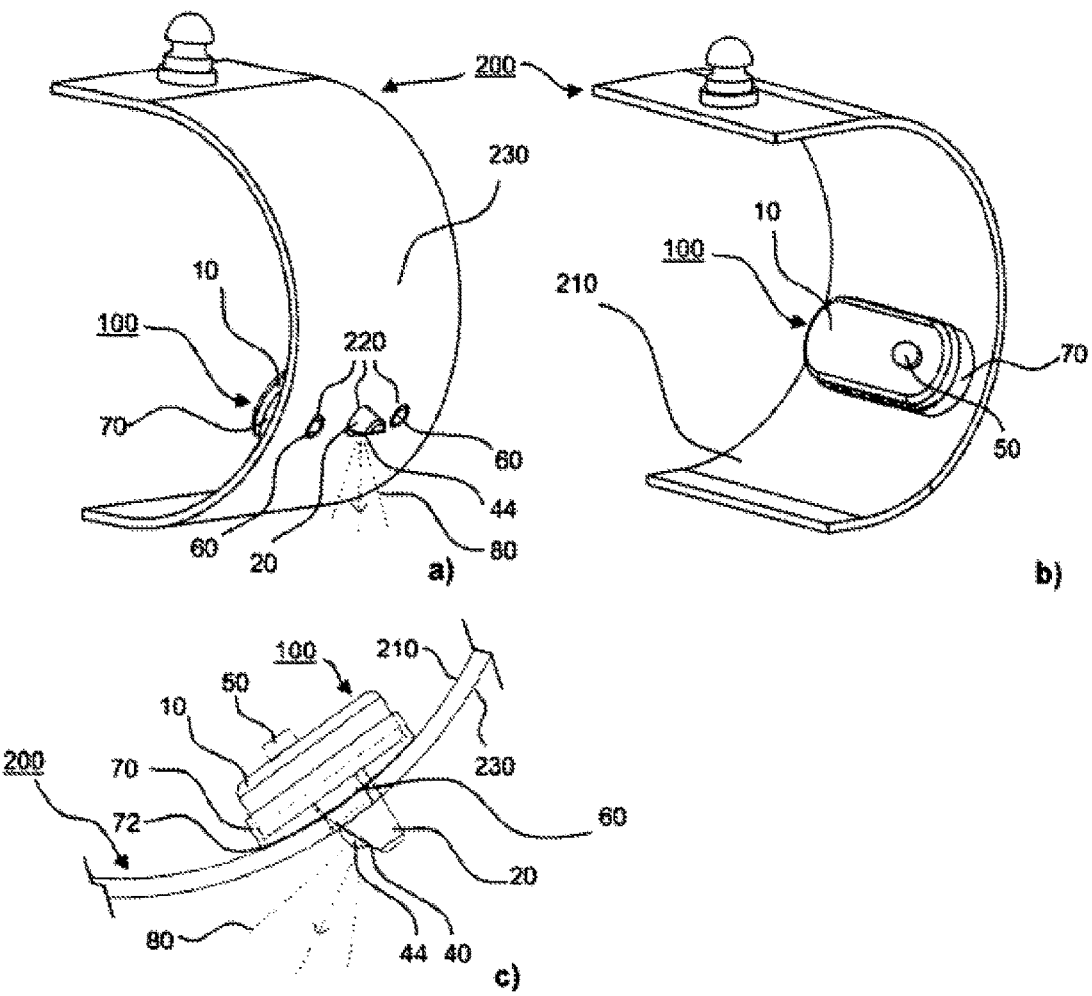
FIG. 5 a retractor blade with attached lighting device with a press switch on the housing's rear side and mounted membrane sheath as intermediate piece, a) in perspective from the front, b) in perspective from the rear, c) in front view.

FIG. 5 depicts a retractor blade 200 of an otherwise not shown surgical instruments with a lighting device 100 disposed on the rear or inner side 210 of the retractor blade. The pin 20 of the lighting device reaches through the fenestration 220 in form of a round through hole of the retractor blade 200. Since the rear side of the depicted retractor blade 210 is rounded and the lighting device has a plane frontal wall area 30 in this embodiment, as in FIG. 1 and FIG. 2, a membrane sheath 70 is disposed for compensation between the surface of the rear side of the blade 210 and the wall area 30 of the lighting device 100. It can be easily seen in FIG. 5c) that the elastic membrane sheath 70 clings with its surface 72 both to the shape of the housing 10 and to the rear side 210 of the retractor blade. The membrane sheath 70 is made of an elastic plastic material. The space between the wall area 30 of the housing 10 and the rear side 210 of the retractor blade is filled or sealed by the membrane material. In this embodiment, the wall area 30 of the lighting device 100 and its associated region of the surgical instrument's part adjoining to the lighting device 100 in the fastening position are not designed in a mirror-inverted manner or positioned in a flush-mounted manner, which is compensated by the membrane sheath 70. At the same time, the membrane sheath 70 encloses the lighting device 100 in a moisture-proof manner, it can optionally have a high coefficient of friction and act adhesively or it can be equipped adhesive or pressure-sensitive adhesive. In this embodiment, the activation of the lighting device 100 is performed via a mechanical pressure key 50 attached to the housing 10. The pin 20 carries a translucent cover 44, under which a LED is located, whose light emission is indicated by dashed lines in FIG. 5c). The depicted retractor blade 200 has in total three fenestrations 220, the one in the middle for the passage of the pin 20 and two side drilled holes on the side, through which the two nubs 60 reach, which serve as clamping protrusions for additional support of the lighting device 100. Alternatively, the fenestrations 220 of the retractor blade 200 may be dimensioned in a way so that only the nubs 60 produce a clamping connection between the lighting device 100 and the retractor blade 200, while the pin 20 is only inserted through the associated fenestration 220. For this plug-in connection of the pin 20 it is produced without excess or with slight undersize compared to the fenestration 220. This preserves the pin. Since the clamping connection is provided by the nubs 60, there is no need for the pin 20 with lens 44 also to be frictionally pressed into the associated fenestration 220 in a force-fit manner. Alternatively, the retractor blade has a multiple of the required fenestrations, which are positioned to each other at some distance, so that the lighting device 100 can be positioned as needed.

Figure 6:
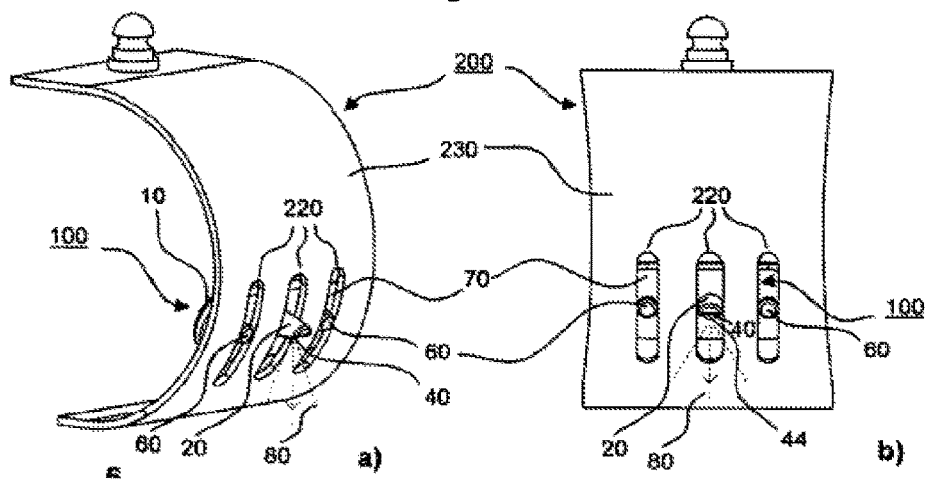
FIG. 6 a retractor blade with slit-shaped fenestration and mounted lighting device with membrane sheath as intermediate piece, a) in perspective, b) in front view.

FIG. 6 depicts a corresponding embodiment as in FIG. 5, but in which the fenestrations 220 are designed as oblong holes. The lighting device 100 is similar to that of FIG. 5. FIG. 6b) shows the embodiment in the front view that is shown in FIG. 6a) in perspective. The fixation of the nubs 60 and optionally also of the pin 20 is carried out slidably via the oblong holes. The emission direction of the illuminant can be changed in this way. The surgeon can carry out this illumination adjustment on the spot in that he arranges the lighting device 100 in the desired position within the oblong holes of the fenestrations 220.

Figure 7:
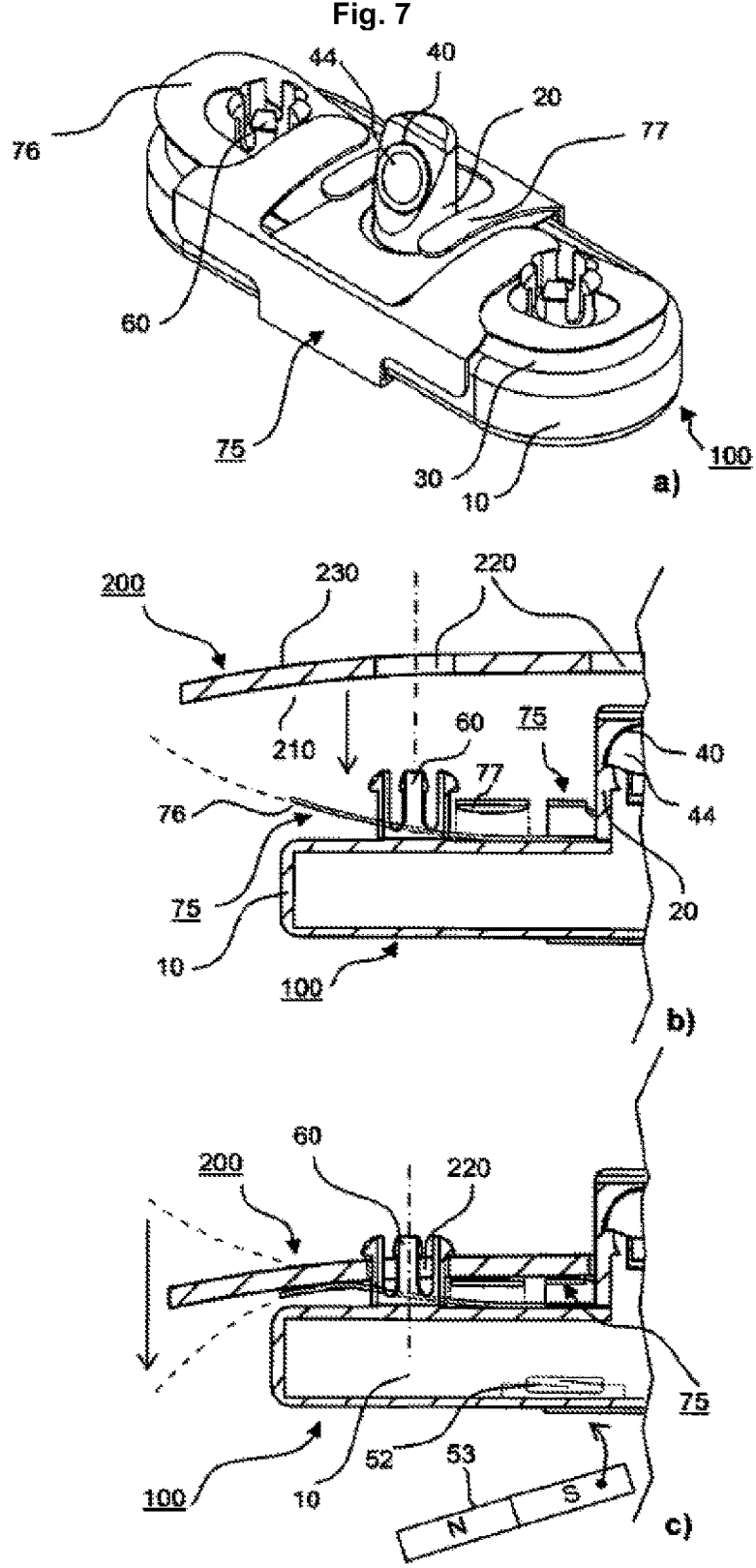
FIG. 7 a further embodiment of the lighting device with mounted spring clip as compensation device for better adaptation to a retractor blade a) in perspective view, b) in partial side view before the installation on a blade, c) in partial side view after the installation on a blade.

FIG. 7 shows an alternative embodiment of the lighting device 100 with fastening projections 60, which are designed as snap-in hooks, and which, as shown in FIG. 7c 1, engage in fenestrations 220 of a retractor blade 200. FIG. 7a) also shows a spring clip 75, which assumes the same function as the membrane sheath 70 in other embodiments. The spring clip 75 may be attached on the wall area 30 of the housing 10 in a locking, snapping or adhesive manner and consists of several metallic longitudinally 76 and transversely 77 extending leaf springs, which—upon attachment of the lighting device 100 on a retractor blade 200—deflect and adapt correspondent to the shape of the surface of the blade and remain in a tensed position, so that the lighting device 100 can also be mounted on uneven instrument surfaces. The spring clip 75 ensures a firm grip and prevents a breaking of the pin and the nubs or the fastening projections, if lateral forces, caused for example by pressing tissue, act on the lighting device. The tense leaf springs 76, 77 then counteract the forces, which act on the lighting device, due to their spring-back properties and their biased storage. The embodiment of the fastening projections 60 with snap-in hooks prevents that the lighting device disengages again from the retractor blade due to the rebounding spring clips 75. Alternatively, the spring clip 75 may be also designed in such a way that it can be fixed laterally on the retractor blade 200 and clamps the lighting device 100 additionally in this way. In this case, there is no need for the design of the fastening projections as snap-in hooks. The activation of the lighting device is carried out again via an internal magnetic switch 52.

FIG. 8 shows a further embodiment of the invention in which a slightly modified lighting device 100 is attached to a retractor blade 200 having an edged, pronged lower section 240. The lighting device 100 is modified such that the pin 20 is located at an anterior front end of the wall area 30 of the housing 10 and one fastening projection 60 and another is arranged at the rear end of the wall area 30 of the housing 10. The light-emitting opening 40 has thus an improved position for the illumination of the surgical field, because it is located as close as possible to the surgical field. The wall 30 of the lighting device 100 has full surface contact with the rear side of the retractor blade 200; the device 100 is optimally adapted to the elongated shape of the retractor blade. The lighting device 100 is attached to the upper half of the retractor blade 200. Because of this, there is sufficient space for the tissue retained by the retractor blade 200 between the prongs of the section 240 and the lighting device 100. The effect of the prongs is not affected by the presence of the housing 10. FIG. 8b) depicts a side view which indicates that the activation of the lighting device is carried out magnetically via an external magnet 53.

Figure 9:
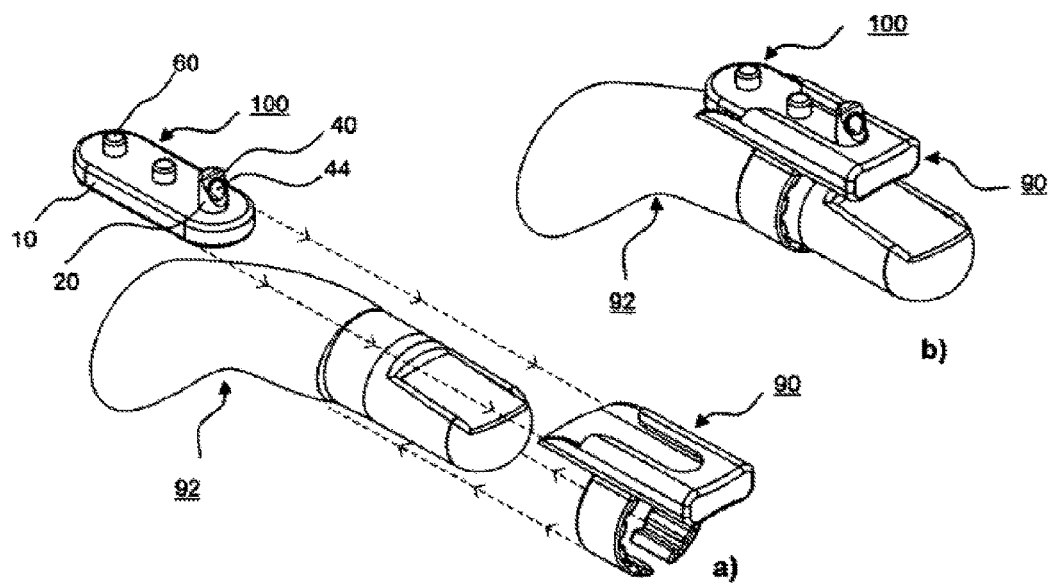
FIG. 9 an embodiment of the lighting device in connection with an adapter ring for the fastening to a human finger a) as exploded view drawing and b) in perspective view.

FIG. 9 depicts the lighting device 100 in combination with an adapter ring 90 for placing on a human finger 92, in FIG. 9a) in an exploded view and in FIG. 9b) in the superimposed position. The adapter ring 90 is designed like a ring and can be fastened to a body part, e.g. to a finger 92, but also to different objects. The ring-shaped part or the ring body carries a box-shaped attachment, into which the lighting device can be slided in and be for example fixed in a plugged manner.

The ring body of the adapter ring 90 (FIG. 9a) has a slot-like opening on its bottom side and is made of an elastic material so that it can be attached to a finger 92 or other body parts with varying diameters. The corrugated form of the ring body's inner side, which is contact with the finger 92, serves also for the adaptation to body parts 92 of varying size and shall additionally prevent a sliding off or slipping off of the adapter ring 90 from the body part 92. The box-shaped attachment of the adapter ring 90 simply serves for the reception of the lighting device 100.

Figure 10:
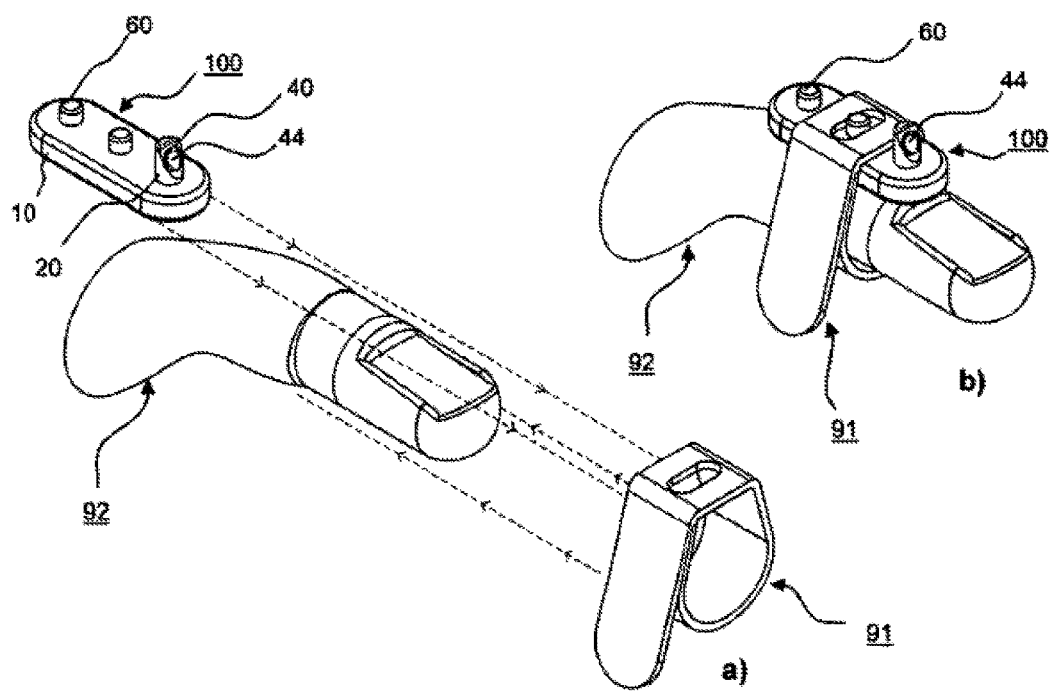
FIG. 10 an embodiment of the lighting device in connection with an adapter strap with hook and loop fastener for the fastening to a human finger a) as exploded view drawing and b) in perspective view.

FIG. 10 depicts in a way of presentation corresponding to FIG. 9 the lighting device 100 in combination with a adapter strap 91, which was wrapped around a finger 92 and fastened by means of a hook and loop fastener. The adapter strap 91 is in particular a Velcro tape with fitting openings for the reception and fixation of the lighting device 100 to a body part 92. It is intended in the embodiment that the lighting device 100 is first plugged and fixed in a fitting opening in the adapter strap 91 and can subsequently be tied around a finger 92 or another, preferably round shaped, object and is fixed by hook and loop fastener.

FIG. 11 depicts a preferred embodiment of the lighting device 100 with a pin 20 and two additional fastening projections 60, wherein one fastening projection 60 is at the same time designed as switch in order to switch the illuminant on and off as well as to optionally regulate its light intensity (brightness or brightness level). The pin 20 is located in the center, the anterior fastening projection 60 serves purely for fastening and the posterior fastening projection 60 is designed as press switch, which serves at the same time for fastening.

FIG. 12 depicts a preferred embodiment of the lighting device 100 with a pin 20 and two additional fastening projections 60 and a solar cell at the bottom side of the housing 10 of the lighting device 100. The solar cell serves for charging an accumulator or a battery inside the housing 10, which then in turn serves as power source for the illuminant in the head of the pin 20.

Figure 13:
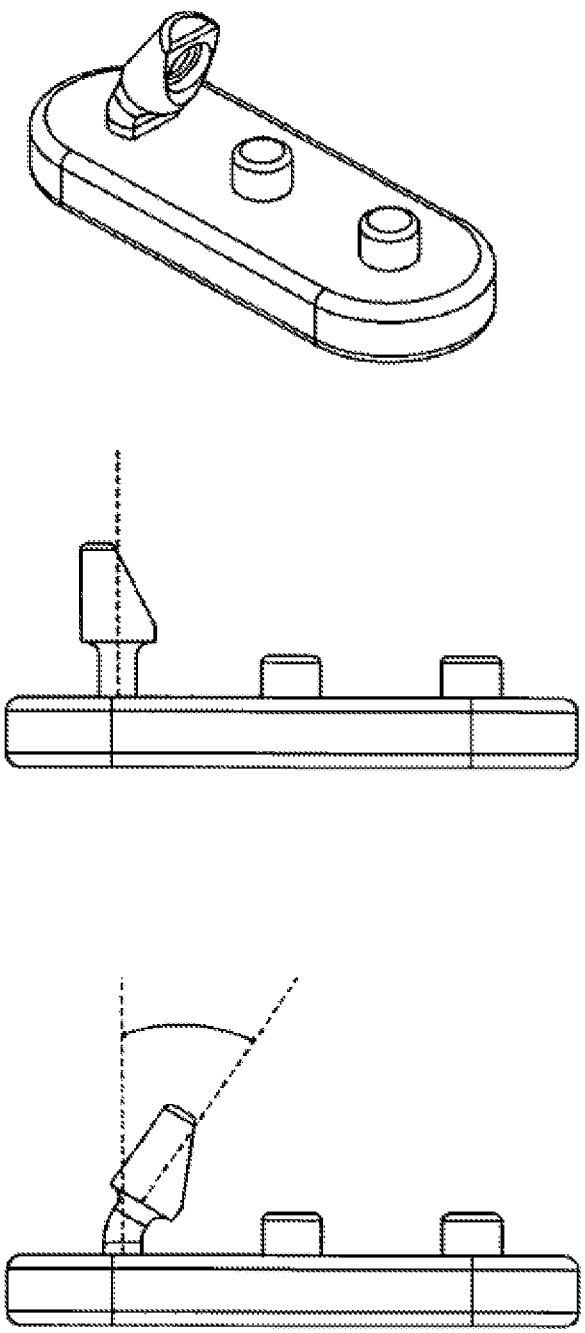
FIG. 13 depicts a preferred embodiment of the lighting device (100) with movable pin (20). The illustration in the middle depicts on the left side the pin (20) in the perpendicular central position, i.e. the axis through the pin (20) stands perpendicular on the plane of the surface of the housing (10) and the light-emitting opening (40) points along the longitudinal axis through the housing (10) of the lighting device (100). In the upper illustration in FIG. 13, the pin (20) bent downwards (or forwards) is illustrated in perspective. In the lower illustration in FIG. 13, the bending of about 45° of the pin (20) bent is illustrated. The pin (20) is just bent downwards or forwards but is not additionally rotated.

The FIGS. 13 to 15 depict embodiments of the lighting device 100 with a movable pin 20 and additional two fastening projections 60. In these embodiments one of the two additional fastening projections 60 is designed as switch. The switch serves for switching the illuminant on and off and further preferred also for adjusting the brightness of the illuminant. In these embodiments with fastening projection 60 designed or not designed as switch a solar cell is preferably integrated into the housing 10 of the lighting device 100, which serves for charging an accumulator or a battery inside the housing 10, wherein this charging can happen in the sterilely packed state through the sterile packaging without the need to unpack the sterilely packed lighting device 100 for charging and to sterilize it again afterwards.

Technical Data

Technical data of the exemplary lighting devices shown in the figures.

| Geometry - Measures and Weight | |
|---|---|
| height: | 8 mm |
| length: | 45 mm |
| width: | 14 mm |
| weight: | 11 g |
| Production Material | |
| material: | biocompatible plastic |
| Operation | |
| minimal operating time (after one year storage at 20° C.): | 120 minutes |
| Energy Source | |
| energy storage | accumulator |
| Light Parameter | |
| light source: | light emitting-diode (SMD format) |
| light color: | warm white |
| light intensity: | 2.300 mcd |
| illumination angle: | 65° |
| infrared radiation: | none |
| color temperature: | 5.000 K |
| CRI-value (Ra-value): | >85 |
| Mechanics | |
| fastening mechanism: | interference fit |

SMD: surface mounted device

LIST OF REFERENCE SIGNS

100 Lighting device
10 Housing
20 Pin
30 Wall area
40 Light-emitting opening
44 Translucent cover/lens
50 Mechanical switch (e.g. press switches, buttons)
52 Magnetic switch
53 Magnet
60 Fastening projection (e.g. nub or snap-in hook)
70 Membrane sheath
71 Fenestration membrane sheath
72 Wall area membrane sheath
75 Spring clip
76 Longitudinal leaf spring
77 Transverse leaf spring
80 Light beam/light cone
90 Adapter ring
91 Adapter strap
92 Body part (e.g. human finger)
200 Surgical instrument (e.g. retractor blade)
210 Rear side of the retractor blade
220 Fenestration
230 Front side of the retractor blade
240 Pronged section

The invention claimed is:
1. A lighting system comprising:
 a surgical instrument comprising at least one through-hole; and
 a lighting device equipped for fastening to the surgical instrument in a fastening position, the lighting device comprising a housing and at least one illuminant located in at least one pin, wherein the at least one pin points outwards from a wall of the housing and is arranged on the housing in a wall area directed towards the surgical instrument in the fastening position, wherein the at least one pin has a light-emitting opening at a distal end of the at least one pin and reaches through the at least one through-hole of the surgical instrument establishing a form-fit or force-fit connection with the at least one through-hole in the fastening position and wherein on the wall area of the housing an additional fastening projection in the form of a stud or a nub is provided for switching the at least one illuminant located in the at least one pin on when the lighting device is fastened on the surgical instrument.

2. The lighting system according to claim 1, wherein the pin is an essentially cylindrical stud.

3. The lighting system according to claim 1, wherein the pin is bendable and/or rotatable.

4. The lighting system according to claim 1, wherein the wall area directed towards the surgical instrument in the fastening position is planar or is shaped to follow a contour of a corresponding wall area of the surgical instrument.

5. The lighting system according to claim 1, wherein the additional fastening projection is a first additional fastening projection, wherein on the wall area of the housing comprises at least one second additional fastening projection that is arranged to engage a suitable holder in the surgical instrument.

6. The lighting system according to claim 1, wherein a solar cell is integrated in the housing and/or that the housing contains an energy supply unit.

7. The lighting system according to claim 1, further comprising a compensation element in between a wall area of the housing and an adjoining wall area of the surgical instrument, in order to balance uneven surfaces of the instrument and in order to increase a strength of the connection between the instrument and the lighting device, or comprising an adapter for the fastening of the lighting device on a body part of a surgeon or an OP-assistant.

8. The lighting system according to claim 1, wherein the at least one through-hole is formed in a thin blade, a shank, a housing, a handle, or an even or grooved formed leg of the instrument.

9. The lighting system according to claim 1, wherein the surgical instrument is a forceps, a clamp, a scalpel, a drill bit, a tubular shaft instrument, a retractor, a blocker or a spreader.

10. The lighting system according to claim 1, wherein the at least one through-hole is in the form of a drilled hole, an oblong hole or an otherwise shaped opening for a form-fit or force-fit connection with the at least one pin of the lighting device.

11. The lighting system according to claim 1, wherein the surgical instrument comprises at least one suitable holder for a fastening projection in the lighting device.

12. The lighting system according to claim 1, comprising at least an adapter for the fixation of the lighting device to a body part or a compensation element in between the wall of the housing of the lighting device and an adjoining wall of the surgical instrument.

13. The lighting system according to claim 1, wherein the at least one through-hole cooperates in a clamping fit, a locking fit, a snap-in fit, a frictional engaged plug-in fit, or a press-fit connection with the at least one pin of the lighting device.

14. The lighting system according to claim 13, wherein the at least one through-hole cooperates in a press-fit connection with the at least one pin of the lighting device.

15. The lighting system according to claim 1, wherein the connection between the at least one through-hole of the surgical instrument and the at least one pin of the lighting device fastens the lighting device to the surgical instrument.

16. The lighting system according to claim 1, wherein the additional fastening projection is arranged to engage a suitable holder in the surgical instrument.

* * * * *